(12) United States Patent
Tittelbach

(10) Patent No.: US 8,357,191 B2
(45) Date of Patent: Jan. 22, 2013

(54) CATHETER HAVING AN APPLICATOR DEVICE FOR LIQUID ACTIVE SUBSTANCES

(75) Inventor: Michael Tittelbach, Nuernberg (DE)

(73) Assignee: Biotronik VI Patent AG, Baar (CH)

( * ) Notice: Subject to any disclaimer, the term of this patent is extended or adjusted under 35 U.S.C. 154(b) by 587 days.

(21) Appl. No.: 12/575,099

(22) Filed: Oct. 7, 2009

(65) Prior Publication Data

US 2010/0094396 A1 Apr. 15, 2010

(30) Foreign Application Priority Data

Oct. 13, 2008 (DE) .......................... 10 2008 042 798

(51) Int. Cl.
*A61M 25/00* (2006.01)
*A61F 2/84* (2006.01)

(52) U.S. Cl. ..................................... 623/1.11; 604/523

(58) Field of Classification Search .................. 604/523, 604/103, 103.5, 101.02, 103.2; 623/1.11, 623/1.42, 1.15, 1.43–1.46; 606/191–192
See application file for complete search history.

(56) References Cited

U.S. PATENT DOCUMENTS

| | | | | |
|---|---|---|---|---|
| 5,368,566 A * | 11/1994 | Crocker | ................... | 604/101.02 |
| 6,364,856 B1 * | 4/2002 | Ding et al. | ............... | 604/103.02 |
| 6,409,716 B1 * | 6/2002 | Sahatjian et al. | ............. | 604/509 |
| 7,229,454 B2 * | 6/2007 | Tran et al. | ..................... | 606/157 |
| 2005/0033402 A1 * | 2/2005 | Cully et al. | .................. | 623/1.11 |
| 2005/0278012 A1 * | 12/2005 | Vonderwalde | ............... | 623/1.11 |
| 2006/0124056 A1 | 6/2006 | Behnisch et al. | | |
| 2007/0048350 A1 * | 3/2007 | Falotico et al. | ............... | 424/423 |
| 2007/0231499 A1 | 10/2007 | Worsham et al. | | |
| 2008/0140177 A1 * | 6/2008 | Hines | ........................... | 623/1.11 |
| 2008/0141932 A1 | 6/2008 | Chen et al. | | |
| 2008/0208310 A1 * | 8/2008 | McDermott et al. | ......... | 623/1.11 |
| 2008/0243068 A1 * | 10/2008 | Ramzipoor et al. | ..... | 604/103.01 |
| 2011/0230952 A1 * | 9/2011 | Kassab et al. | ................ | 623/1.11 |

FOREIGN PATENT DOCUMENTS

| EP | 1 325 758 | 7/2003 |
|---|---|---|
| WO | WO 2007/008829 | 1/2007 |

OTHER PUBLICATIONS

Search Report for Corresponding European Patent Application No. 09170267.0-1257, issued on Feb. 8, 2010.
German Patent Office, Search Report for Priority German Application No. 10 2008 042 798.5, Issued Oct. 14, 2009.

* cited by examiner

*Primary Examiner* — Kevin C Sirmons
*Assistant Examiner* — Michael J Anderson
(74) *Attorney, Agent, or Firm* — Greer, Burns & Crain, Ltd.

(57) ABSTRACT

The invention relates to a catheter, in particular an endovascular catheter, having an applicator device for liquid active substances for applying same to an active substance storage zone mounted on the catheter.

21 Claims, 5 Drawing Sheets

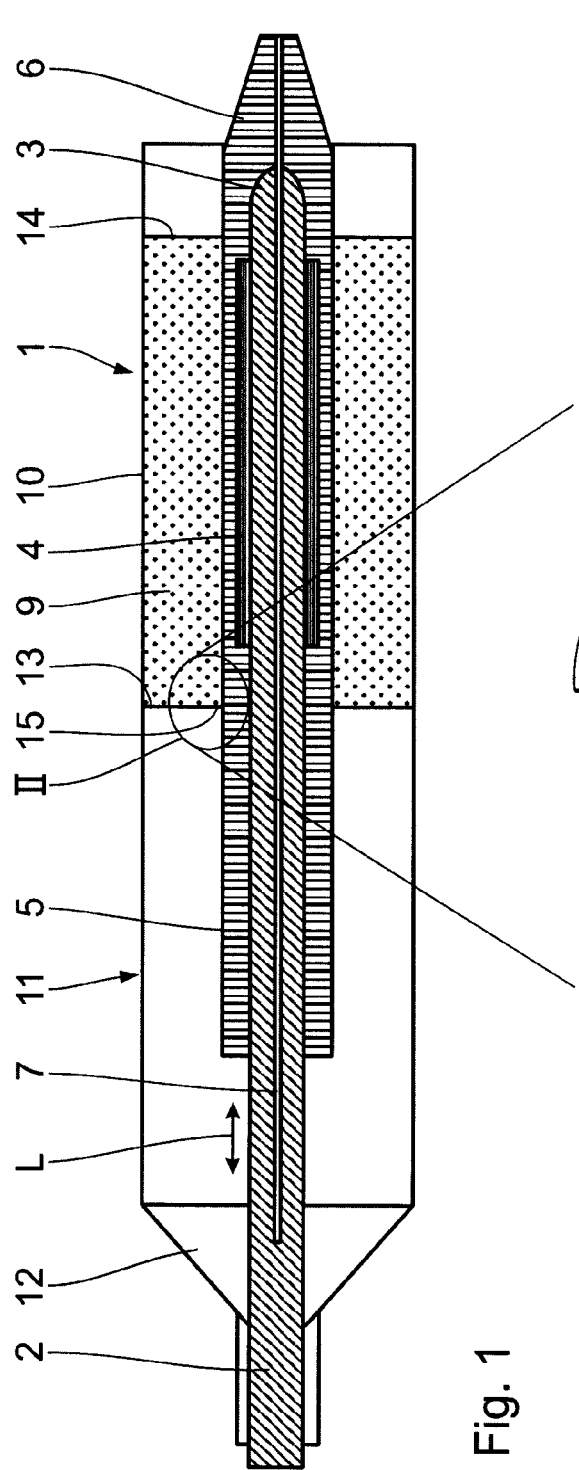
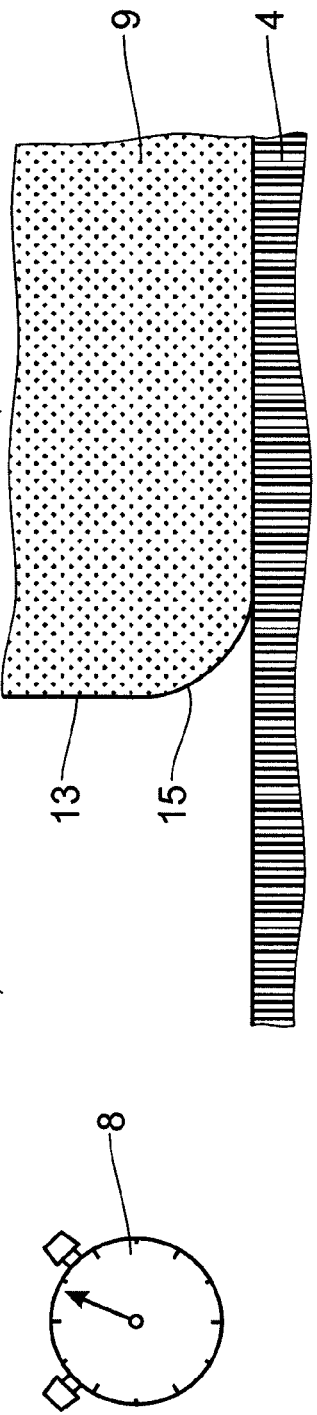
Fig. 1
Fig. 2

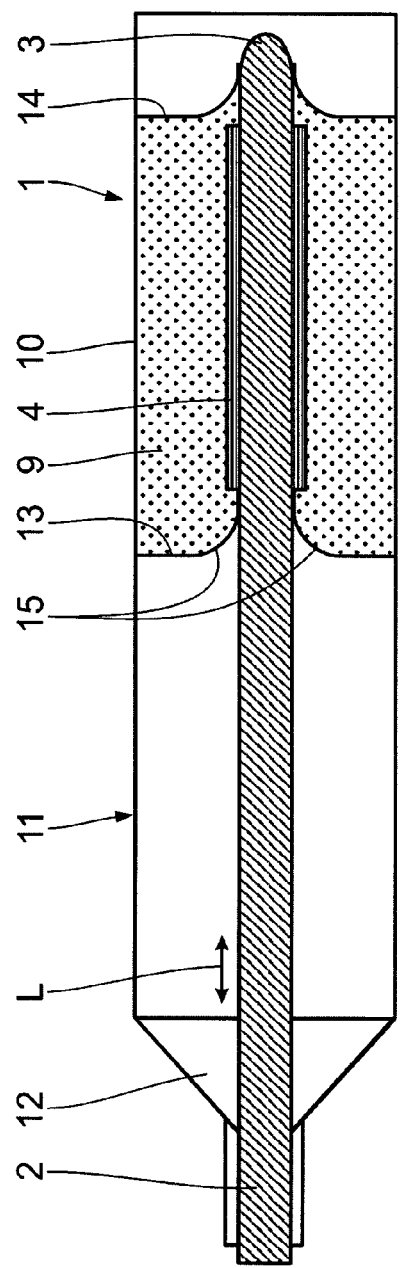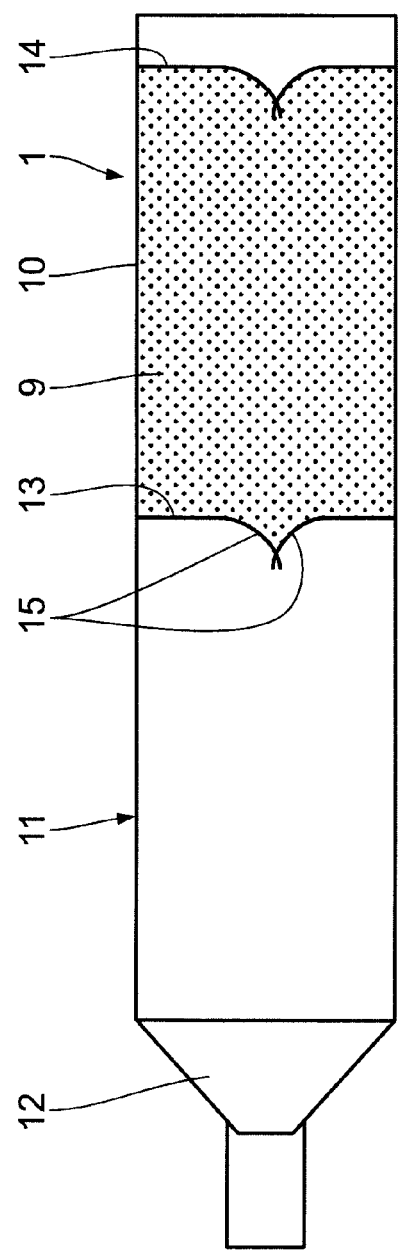

CATHETER HAVING AN APPLICATOR DEVICE FOR LIQUID ACTIVE SUBSTANCES

FIELD OF INVENTION

The invention relates to a catheter, in particular an endovascular catheter, having an applicator device for liquid active substances.

BACKGROUND OF THE INVENTION

With regard to the background of the invention, it is noted that catheters having so-called drug-eluting stents are known from the prior art in which only solids are used as pharmaceutical active substances. Typical approaches for providing an active substance on or in stents involve incorporation of the active substance into a polymer support, introduction into a porous surface, or integration into active substance depots on the stent. These technical designs are tailored to solids, since for mechanical reasons liquid substances cannot be permanently applied to the stent surface. In addition, compounds in a liquid substance in the stent cause fundamental difficulties with regard to stability under storage. For example, drying phenomena or demixing effects may occur.

Approaches to coating medical implants, in particular stents, with liquids are known from US 2006/0124056 A1 or EP 1 325 758 A2. The first-referenced document discloses a device for applying active substances to surfaces of medical implants, in particular stents, composed of a base station and an exchangeable cartridge. A holder for the stents is provided on the cartridge, by means of which the active substances are sprayed via a nozzle onto the surface of the stent. A drive unit is provided on the base station which moves the stent holder and the nozzle relative to one another, the aim being to ensure defined wetting of the stents with liquid active substance.

In the second-referenced document, the aim is to improve the dosing accuracy for the liquid medicament on the stent by applying a potential difference between the spray unit and the stent.

A problem with the above approaches is that, immediately before placement of the catheter together with the stent, a surgeon must coat the stent with the active substance solution. For this purpose the stent has a porous surface onto which a solution of alcohol and rapamycin, for example, is sprayed. This is a complicated and time-consuming procedure in the surgical environment, in which the dosing of the liquid active substance is very imprecise.

SUMMARY OF THE INVENTION

On this basis, the feature of the invention is to design a catheter having an applicator device for liquid active substances, such that the latter may be applied to the active substance storage zone in simple process steps and in a short period of time, using a defined active substance dose immediately before the surgical use.

This feature is achieved by the features of Claim 1. Accordingly, the applicator device which surrounds the catheter body in the region of the active substance storage zone with a protective cover has an active substance container, open or to be opened toward the protective cover, with flexible boundary walls on both sides of the active substance storage zone which provide a seal with respect to the protective cover and, after the protective cover is removed, with respect to the catheter body. In this manner the active substance storage zone may be impinged on by the active substance present in the active substance container after the protective cover is removed. The active substance container may be removed from the catheter after a sufficiently long exposure of the active substance storage zone to the active substance liquid. The liquid present in the active substance container is largely retained therein, thus allowing subsequent disposal of the active substance container together with the applicator device. The active substance storage zone on the catheter itself must be provided with an accurately determinable dose of the active substance by impingement over a defined period of time. The entire administration process may be performed very easily and in a comparatively short time, so that the catheter having the applicator device according to the invention is particularly suited for applying the active substance immediately before the surgical use of the catheter. The term "active substance" refers to all pharmaceutically active formulations, such as active substances in pure form, solutions of active substances, etc.

The described "active substance storage zone" generally involves the stents, mentioned above in the introductory description, which may be loaded with active substance. In addition, catheters for expanding a stenosis are known in which only the distal end of the catheter together with a balloon provided at that location is guided to the constricted site, and the stenosis is expanded by dilating the balloon. In conjunction with the present invention, the balloon itself, i.e., without a stent resting thereon, may function as an active substance storage zone.

The active substance applied immediately before the surgical use is maintained on the stent or balloon in the sense of "storage" until the positioning of the stent or balloon of the catheter is completed.

DESCRIPTION OF THE DRAWINGS

Preferred refinements of the catheter are stated in the dependent claims. The features, particulars, and advantages thereof are provided in the following description and the exemplary embodiments of the subject matter of the invention, with reference to the accompanying figures, which show the following:

FIG. 1 shows a schematic sectional axial view of the distal end of a catheter having an applicator device, in a stored state;

FIG. 2 shows an enlarged detailed section according to detail II in FIG. 2;

FIG. 3 shows an illustration analogous to FIG. 1, in a loading state with the protective cover removed;

FIG. 4 shows a schematic axial view of the applicator device in a disposal state, removed from the catheter;

DETAILED DESCRIPTION OF THE INVENTION

Figure 5:
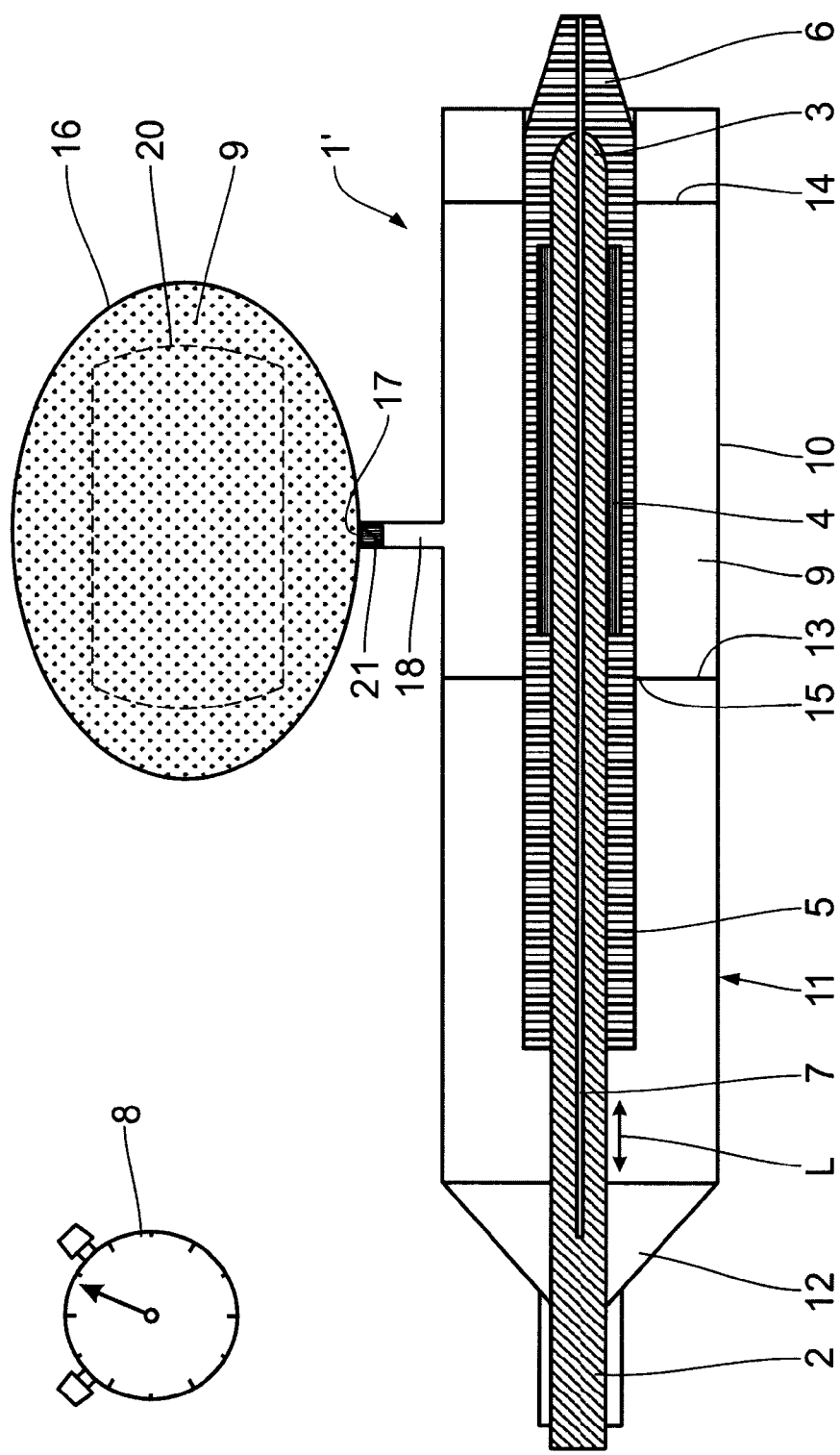
FIG. 5 shows an illustration analogous to FIG. 1 of a catheter having an applicator device, in an alternative embodiment in the stored state.

A catheter having an applicator device designated collectively as reference numeral 1 is described in a first embodiment in the stored state, with reference to FIGS. 1 and 2. The catheter has an elongated catheter body 2, of which only the region upstream from the distal end 3 to be inserted into the body of a patient is illustrated. Upstream from this distal end 3 a stent 4 is crimped onto the balloon (not illustrated) of the catheter body 2 in a customary manner, and is covered by a protective cover 5. The latter is composed of a hose-like main section to which a shrink tubing piece 6 is distally fastened for attachment of a wire 7 in the protective cover 5. The wire is inserted into a wire lumen (not illustrated in greater detail) of the catheter body 2 to provide sufficient support for the protective cover 5. The protective cover 5 projects beyond the stent 4 on both sides in longitudinal direction L of the catheter body 2.

The applicator device 1 for a liquid active substance 9 is placed over the protective cover 5. The integral component of this applicator device 1 is an active substance container 10 which is open toward the protective cover 5, and which in the form of an annular vessel is provided around the protective cover 5. The active substance container 10 is mounted on a long, sleeve-like holder 11 which at its proximal end rests on the catheter body 2 by means of a fixation cone 12. At the distal end the holder 11 is detachably fastened to the protective cover 5 in a suitable manner.

At both the proximal and distal ends the active substance container 10 has an annular circumferential, flexible boundary wall 13, 14, which with its radially inwardly facing end face in the form of a sealing lip 15 in each case makes sealing contact with the circumference of the protective cover 5 to prevent entry of liquid. As shown in the enlarged illustration according to FIG. 2, the sealing lip 15 of the boundary walls 13, 14 may be flexibly bent to improve the sealing contact.

In the stored state of the catheter together with applicator device 1 shown in FIG. 1, the stent is separated from the active substance 9 in the active substance container 10 by means of the protective cover 5. After manufacture, the entire device together with the liquid active substance 9 may be sterilized by radiation sterilization, for example. It is important in particular that the activity of the active substance 9 is not impaired by radiation sterilization.

To dose the stent 4 with the active substance 9, during a surgical operation the protective cover 5 is pulled from the catheter body 2 and the applicator device 1 in the distal direction, whereby the boundary walls 13, 14, designed in the manner of a septum, for example, slide along the surface of the protective cover 5 while maintaining a seal. After the protective cover 5 is removed, the boundary walls 13, 14 form a seal against the catheter body 2 on both sides of the stent 4, so that in this loading state, as shown in FIG. 3, the active substance 9 is then able to act on the stent 4 and dose same. By use of a stopwatch 8 associated with the catheter together with the applicator device 1 which may be integrated into a surgical setup, for example, a defined time for impingement of the stent 4 with the liquid active substance 9 may be specified. The stopwatch 8 may be automatically started upon removal of the protective cover 5. An alarm may be generated after the defined impingement time has elapsed. The surgeon then removes the entire holder 11 together with the active substance container 10 from the distal end 3 of the catheter body 2, whereby the proximal boundary wall 13 wipes the stent 4 and thus entrains excess active substance liquid.

As shown in FIG. 4, the boundary walls 13, 14 are designed in such a way that they provide an outwardly directed seal for the active substance container 10 also after the applicator device 1 is removed from the catheter, thus allowing clean disposal of the liquid active substance 9 together with the applicator device 1.

Figure 6:
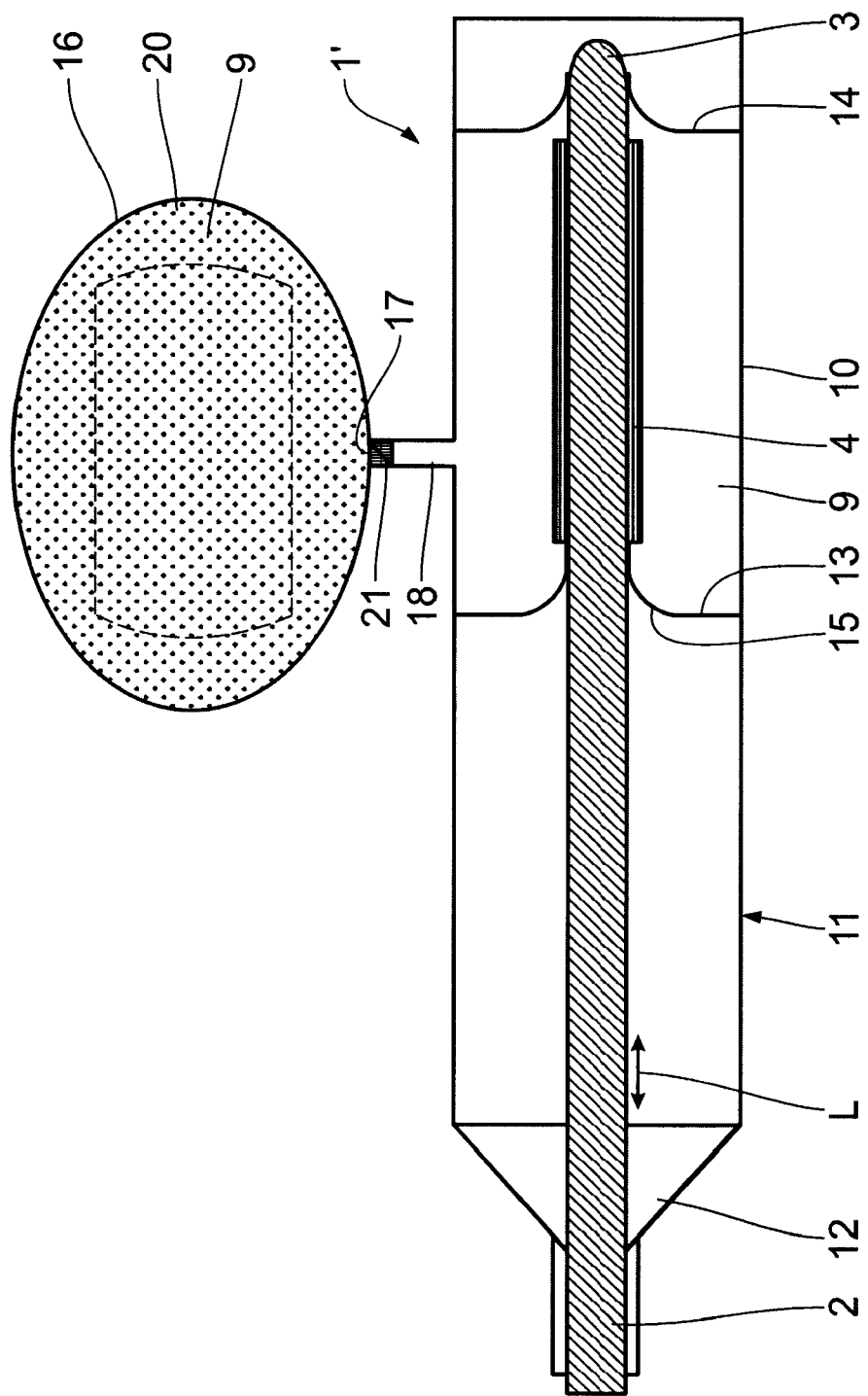
FIG. 6 shows an illustration analogous to FIG. 5 in an intermediate state, after removal of the protective cover.
Figure 7:
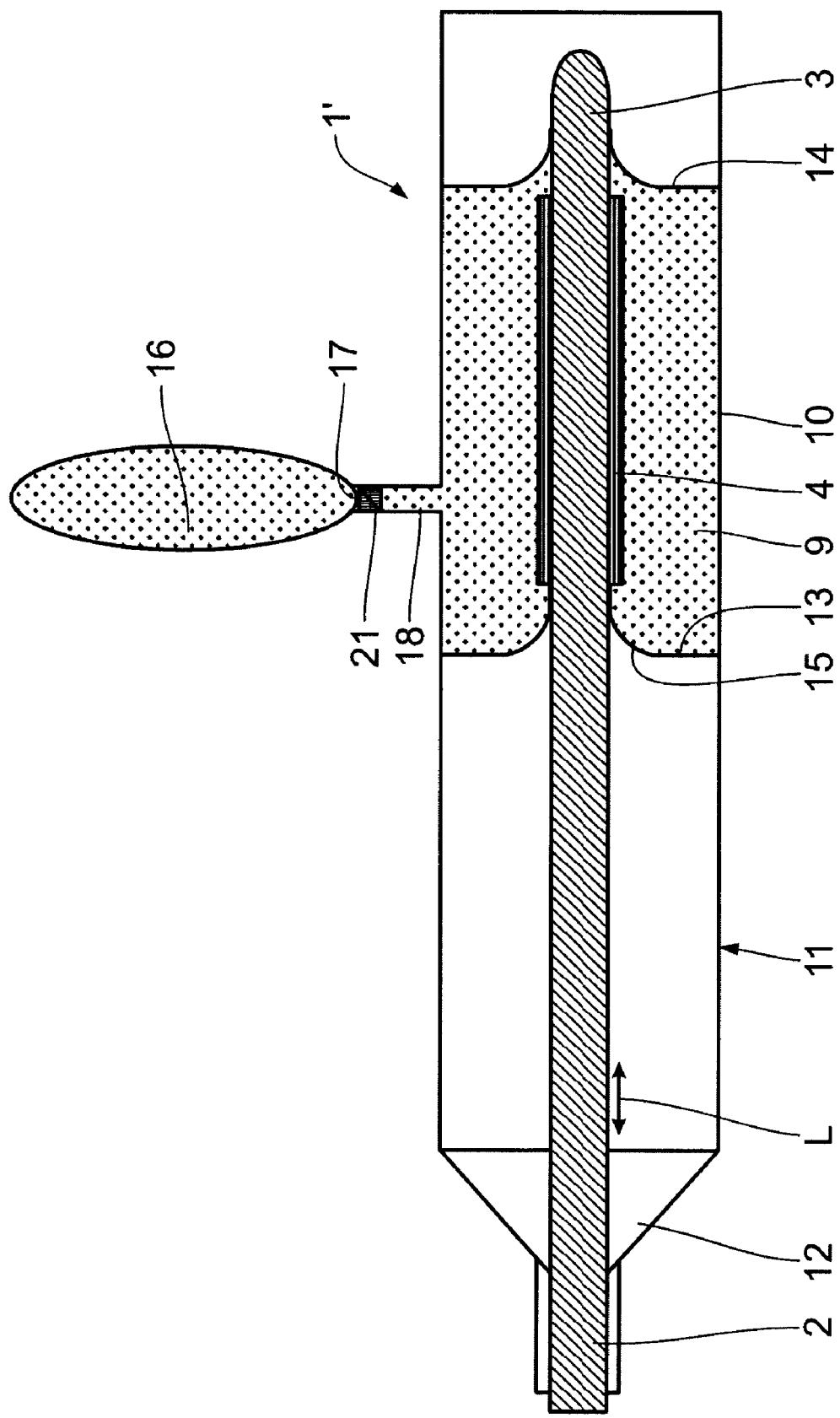
FIG. 7 shows an illustration analogous to FIG. 5 in the loading state, with active substance liquid transferred from the reservoir into the active substance container.

FIGS. 5 through 7 show one alternative embodiment of a catheter having an applicator device 1'. The actual catheter together with the catheter body 2, stent 4, and protective cover 5 as well as the basic configuration of the applicator device 1' together with the active substance container 10 and holder 11 are unchanged from the exemplary embodiment according to FIGS. 1 through 4. In this regard, matching components are provided with identical reference numerals, and reference may be made to the description for the cited figures.

In contrast to the previous exemplary embodiment, the applicator device 1' is provided with a separate reservoir 16 which is designed as a flexible pouch and is closed off by a tearable membrane 17. The reservoir 16 is connected via a hose 18 to the active substance container 10, which is still empty in the stored state according to FIG. 5.

The present configuration allows the active substance 9 to be produced under sterile conditions and then filled into the sterile reservoir 16. Subsequent sterilization of the reservoir 16 containing the active substance 9 is then no longer necessary, so that radiation sterilization which could possibly impair the active substance may be dispensed with. As a last step, the entire system may be sterilized, for example by gas sterilization using ethylene oxide. It is sufficient to provide the reservoir 16 with a gas-tight design.

For dosing the stent 4 with the active substance 9, in the same manner as for the exemplary embodiment according to FIGS. 1 through 4 the protective cover 5 is pulled from the applicator device 1', and the sealing lips 15 of the boundary walls 13, 14 once again form a tight seal with respect to the catheter body 2.

The pouch-like reservoir 16 is then pressurized by hand, the membrane 17 is torn, and the active substance 9 passes through the hose 18 and into the active substance container 10, which once again allows the stent 4 to be impinged on by the active substance over a defined period of time.

The impingement time may once again be measured using the stopwatch 8 which is schematically indicated in FIG. 7.

After the impingement time has elapsed, the entire applicator device 1' together with the reservoir 16 is removed from the distal end 3 of the catheter body 2, analogously to the exemplary embodiment according to FIGS. 1 through 4, and the active substance 9 is once again entrained and wiped from the stent 4. The catheter may then be directly placed, and the stent 4 loaded with active substance may be applied.

As indicated by the dashed lines in FIGS. 5 and 6, a rigid interior container 20, for example in the form of a glass ampoule, may also be provided inside the pouch-like reservoir 16 for storing the active substance 9 if the active substance needs to be optimally protected from degradation, for example as the result of a sterilization process using ethylene oxide. The glass ampoule may be broken through the pouch from the outside, causing the active substance 9 to spill into the pouch and also into the active substance container 10.

A filter 21 is provided in the hose 18 so that glass and other particles which may possibly result from breakage of the glass ampoule are retained in the reservoir 16.

It is noted that the active substance container may also be designed as a tubular bag placed around the protective cover in the manner of a ring, whereby the wall of the tubular bag adjoining the protective cover is torn out upon removal of the cover to allow the active substance to access the stent. Lastly, it is noted that the applicator device according to the invention may be used with any type of medical device resting on a catheter, whether it is permanently or temporarily introduced into the body, such as a balloon, for example, for expanding a stenosis, with omission of the actual stent, and the device may thus be loaded with an active substance. This is described by the active substance storage zone characterized in this manner.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A catheter, in particular an endovascular catheter, having an applicator device for liquid active substances for applying the liquid active substances to an active substance storage zone provided on the catheter, comprising:
   an elongated catheter body having a distal end;
   the active substance storage zone located on the catheter body upstream from the distal end;
   a removable protective cover which surrounds the active substance storage zone; and
   wherein the applicator device which surrounds the catheter body together with the protective cover in the region of the active substance storage zone, having an active substance container open toward the protective cover such that after the protective cover is removed, immediately before the catheter is used the active substance storage zone is impinged on by the active substance present in the active substance container.

2. A catheter according to claim 1, characterized in that the applicator device is provided with flexible boundary walls on both sides of the active substance storage zone which provide a seal with respect to the protective cover and, after the protective cover is removed, with respect to the catheter body.

3. A catheter according to claim 1, characterized in that the applicator device has a sleeve-like holder which
   accommodates the active substance container,
   is attached at a proximal end to the catheter body, and
   rests with a distal end on the protective cover, with the distal end exposed.

4. A catheter according to claim 2, characterized in that the boundary walls are formed by a septum.

5. A catheter according to claim 1, characterized in that the boundary walls are designed in such a way that the active substance container remains sealed to the outside, also after the applicator device is removed from the catheter body.

6. A catheter according to claim 1, characterized in that the active substance container is an annular hose which surrounds the protective cover together with the active substance storage zone, and whose inner wall facing the protective cover may be removed when the protective cover is pulled off.

7. A catheter according to claim 1, characterized in that the catheter is configured to be completely sterilized together with the applicator device filled with active substance.

8. A catheter according to claim 1, characterized by a separate reservoir which is filled with active substance, and which is configured to be connected to the active substance container for the applicator device for filling the active substance into the active substance container.

9. A catheter according to claim 8, characterized in that a hose is provided for the connection between the reservoir and the active substance container, and a particle filter provided in the hose.

10. A catheter according to claim 8, characterized in that the reservoir is closed off by a tearable membrane.

11. A catheter according to claim 8, characterized in that the reservoir is configured as a pouch.

12. A catheter, according to claim 11, characterized in that a rigid interior container which may be broken open is provided in the pouch-like reservoir.

13. A catheter according to claim 1, characterized in that the active substance storage zone is formed by one of a stent or a dilatable balloon on the catheter.

14. A catheter according to claim 1, characterized in that a stopwatch for measuring the time that the catheter is impinged on by the active substance is associated with the applicator device.

15. A catheter according to claim 8 wherein the separate reservoir contains active substance is produced under sterile conditions and is therefore sterile for filling into the reservoir.

16. A catheter according to claim 2 wherein the boundary walls have a sealing lip facing the protective cover.

17. An endovascular catheter, having an applicator device for liquid active substances for applying same to an active substance storage zone provided on the catheter, the applicator device comprising:
   an elongated catheter body having a distal end and having flexible boundary walls;
   the active substance storage zone located on the catheter body upstream from the distal end;
   a removable protective cover which encloses the active substance storage zone;
   wherein the applicator device surrounds the catheter body together with the protective cover in the region of the active substance storage zone, having an active substance container open toward the protective cover such that the after the protective cover is removed, immediately before the catheter is used the active substance storage zone is impinged on by the active substance present in the active substance container; and
   a separate reservoir configured to be filled with an active substance and configured to be connected before application to the active substance container for delivering the active substance into the active substance container.

18. A catheter comprising:
   an elongated catheter body having a distal end;
   a stent surrounding a portion of the catheter body;
   a removable protective cover surrounding the stent and at least a portion of the catheter body;
   an active substance storage container holding a liquid active substance, the active substance storage container defined between a sleeve-like cover, the removable protective cover, and by opposing flexible boundary walls that extend between the sleeve-like cover and the removable protective cover, whereby when the removable cover is removed the active substance held in the active substance container impinges upon the stent to dose the stent with the liquid active substance.

19. A stent as defined by claim 18 wherein the opposing flexible boundary walls each have a sealing lip in sealing contact with the protective cover and that maintains a sealing contact with the protective cover as the protective cover is slidingly removed from the catheter and stent, the flexible boundary walls sealing lips sealingly engaging the elongated catheter body following removal of the protective cover wherein the liquid active substance is contained.

20. A stent as defined by claim 18 wherein:
   the protective cover has a generally annular shape and completely surrounds an annular perimeter of the catheter elongated body and the stent;
   the sleeve-like cover has a generally annular shape and completely surrounds a perimeter of the protective cover;
   the opposing flexible boundary walls span the sleeve-like cover and the protective cover in a radial direction that is normal to a longitudinal direction of the catheter body; and,
   the opposing flexible boundary walls are positioned up-stream and down-stream from the stent in the longitudinal direction of the catheter body whereby when the liquid active substance is impinged upon the stent after removal of the protective cover the entire length of the stent is exposed to the liquid active substance.

21. A stent as defined by claim 18 wherein:

the protective cover has a hose-like main section that projects beyond first and second ends of the stent in a longitudinal direction of the catheter body;

the sleeve-like cover has a fixation cone at a proximal end resting on the catheter body, and the sleeve-like cover has a distal end that is detachably fastened to the protective cover; and, the protective cover has an end piece that extends beyond the sleeve-like cover distal end, the protective cover configured for sliding removal from the catheter body and stent by sliding removal along the longitudinal direction of the catheter body through the sleeve-like cover distal end.

* * * * *